United States Patent
Kosugi et al.

(10) Patent No.: US 8,631,684 B2
(45) Date of Patent: Jan. 21, 2014

(54) WATER LEAKAGE CHECKING APPARATUS

(75) Inventors: Aiko Kosugi, Sagamihara (JP); Akihisa Ogawa, Hachioji (JP); Masahiko Tomita, Hachioji (JP); Yoshitomo Yaguchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/618,297

(22) Filed: Sep. 14, 2012

(65) Prior Publication Data

US 2013/0008233 A1  Jan. 10, 2013

Related U.S. Application Data

(63) Continuation of application No. PCT/JP2012/056983, filed on Mar. 19, 2012.

(51) Int. Cl.
 *G01M 3/28* (2006.01)
(52) U.S. Cl.
 USPC ............................ 73/40.5 R; 73/49.2; 73/49.3
(58) Field of Classification Search
 USPC .................................... 73/40.5 R, 49.2, 49.3
 See application file for complete search history.

(56) References Cited

U.S. PATENT DOCUMENTS

| 2007/0185385 A1* | 8/2007 | Noguchi et al. .............. 600/132 |
| 2009/0105540 A1* | 4/2009 | Kawata et al. ................ 600/118 |
| 2010/0071736 A1 | 3/2010 | Watanabe et al. |

FOREIGN PATENT DOCUMENTS

| JP | 11-276434 | 10/1999 |
| JP | 2009-172228 | 8/2009 |
| JP | 2010-035936 | 2/2010 |
| JP | 2010-075267 | 4/2010 |

* cited by examiner

*Primary Examiner* — Hezron E Williams
*Assistant Examiner* — Paul West
(74) *Attorney, Agent, or Firm* — Scully, Scott, Murphy & Presser, P.C.

(57) ABSTRACT

A water leakage checking apparatus includes: a plurality of attachment portions for attaching an endoscope; a water leakage sensing portion that communicates with the plurality of attachment portions and simultaneously carries out a plurality of items of a water leakage check menu; and an endoscope information reading portion that reads endoscope information from the endoscope. Also, the water leakage checking apparatus includes: a control portion that determines an item of the water leakage check menu based on the read endoscope information, assigns the determined item of the water leakage check menu to one of the plurality of attachment portions, and outputs attachment portion identifying information for identifying the assigned one of the attachment portions; and a notifying portion that notifies the attachment portion identifying information outputted from the control portion.

7 Claims, 14 Drawing Sheets

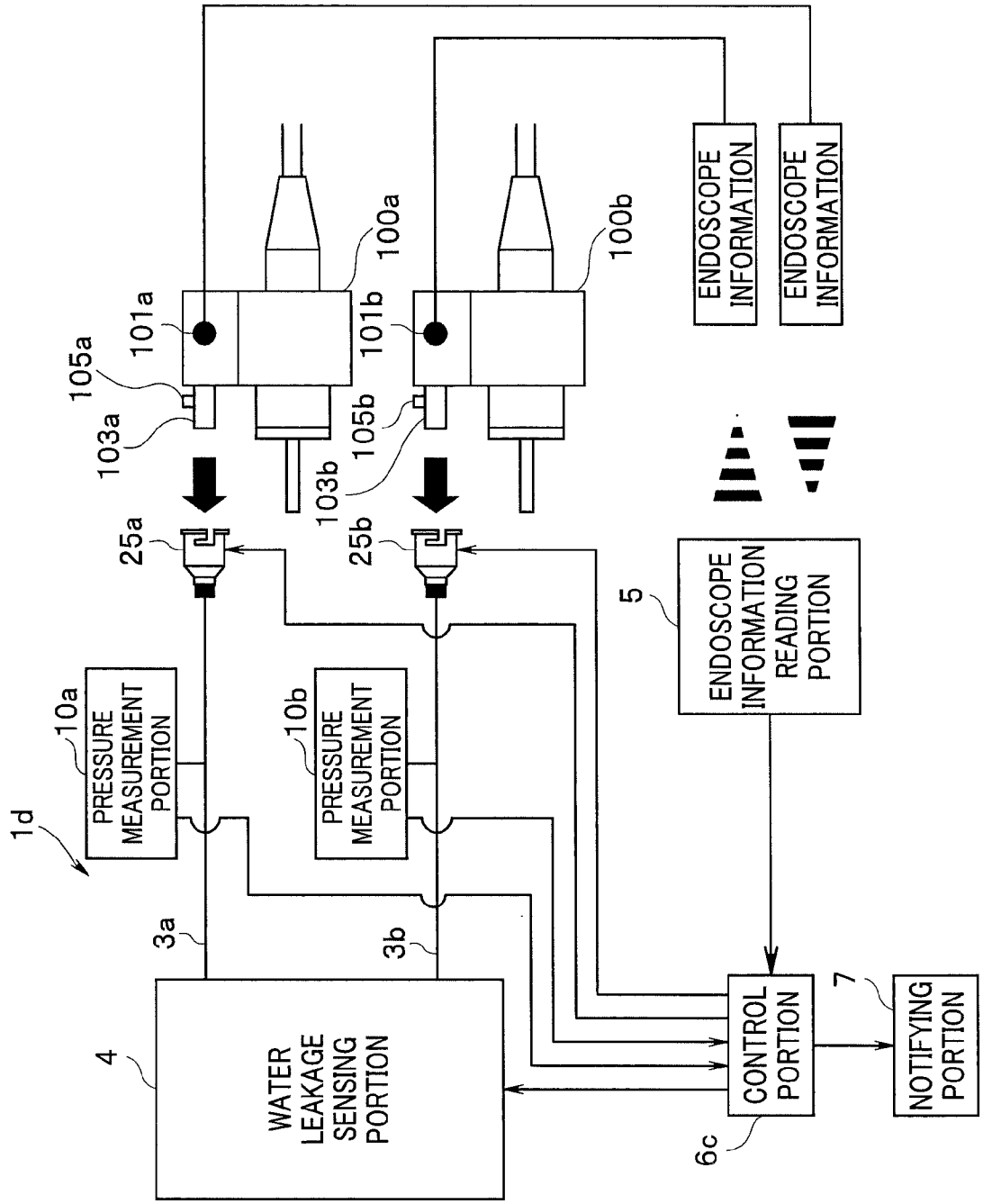

WATER LEAKAGE CHECKING APPARATUS

CROSS REFERENCE TO RELATED APPLICATION

This application is a continuation application of PCT/JP2012/056983 filed on Mar. 19, 2012 and claims benefit of Japanese Application No. 2011-082170 filed in Japan on Apr. 1, 2011, the entire contents of which are incorporated herein by this reference.

BACKGROUND OF THE INVENTION

1. Field of the Invention

The present invention relates to water leakage checking apparatuses, and more particularly, to a water leakage checking apparatus which can simultaneously carry out a plurality of items of a water leakage check menu.

2. Description of the Related Art

Conventionally, in an endoscope used for a purpose of in-body check and treatment, debris adheres not only to an outer surface of an insertion portion inserted in a body, but also to insides of endoscope conduits such as an air/water feed conduit, a suction conduit, and a conduit for inserting a treatment instrument. For this reason, cleaning and disinfection are necessary not only for the outer surface of the endoscope, but also for the insides of the endoscope conduits. Examples of conventional endoscope cleaning/disinfecting apparatuses which clean and disinfect endoscopes include an endoscope cleaning/disinfecting apparatus described in Japanese Patent Application Laid-Open Publication No. 11-276434.

Also, an endoscope cleaning/disinfecting apparatus includes a water leakage checking apparatus for, before cleaning and disinfection, carrying out water leakage checking to make sure that an air-leak hole or the like is not formed, namely, a water leakage part is not formed on inside of an endoscope.

Conventional water leakage checking apparatuses have only a single attachment portion to which an endoscope is attached, and the water leakage checking has been carried out for only a single endoscope. In order to improve working efficiency, it is preferable that water leakage checking be simultaneously carried out for a plurality of endoscopes. Thus, it is conceived that a plurality of attachment portions are provided in a conventional water leakage checking apparatus to allow a plurality of endoscopes to be attached.

SUMMARY OF THE INVENTION

A water leakage checking apparatus according to an aspect of the present invention includes: a plurality of attachment portions for attaching an endoscope; a water leakage sensing portion that communicates with the plurality of attachment portions and simultaneously carries out a plurality of items of a water leakage check menu; an endoscope information reading portion that reads endoscope information from the endoscope; a control portion that determines an item of the water leakage check menu based on the endoscope information, assigns a determined item of the water leakage check menu to one of the plurality of attachment portions, and outputs attachment portion identifying information for identifying an assigned attachment portion; and a notifying portion that notifies the attachment portion identifying information outputted from the control portion.

BRIEF DESCRIPTION OF THE DRAWINGS

FIG. 9 is a diagram showing a configuration of a water leakage checking apparatus according to a fifth embodiment.

DETAILED DESCRIPTION OF THE PREFERRED EMBODIMENTS

Embodiments of the present invention will now be described with reference to the drawings.

First Embodiment

Figure 1:
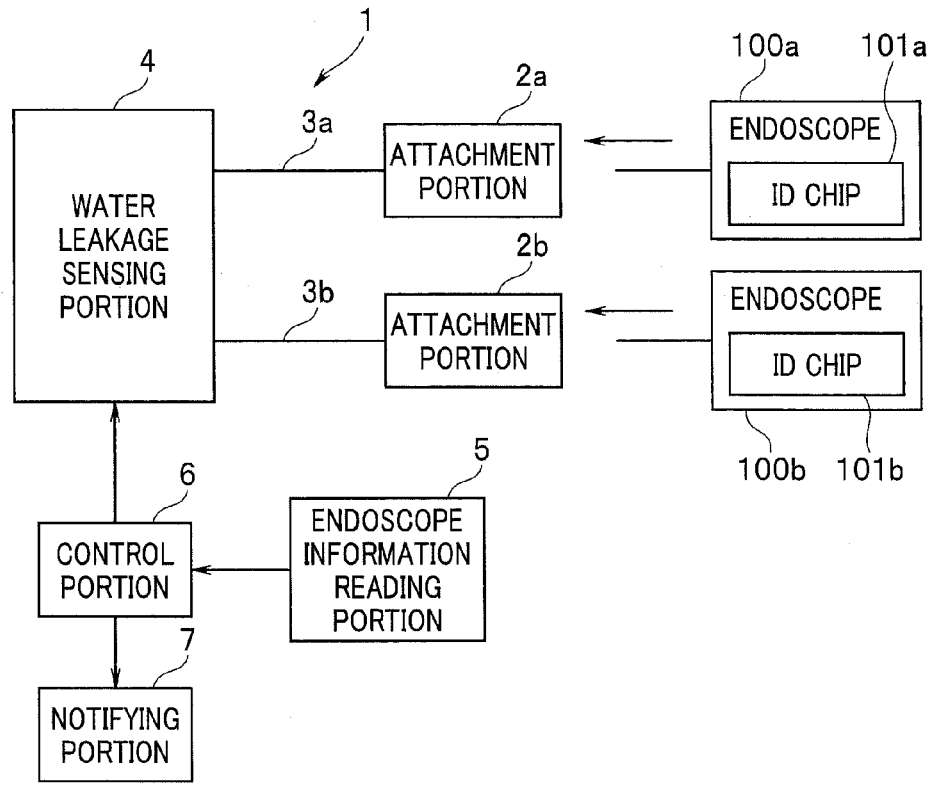
FIG. 1 is a diagram showing a configuration of a water leakage checking apparatus according to a first embodiment.

FIG. 1 is a diagram showing a configuration of a water leakage checking apparatus according to a first embodiment.

As shown in FIG. 1, a water leakage checking apparatus 1 includes a plurality of, here, two attachment portions 2a and 2b, a plurality of, here, two conduits 3a and 3b, a water leakage sensing portion 4, an endoscope information reading portion 5, a control portion 6, and a notifying portion 7. Although the water leakage checking apparatus 1 includes the two attachment portions 2a and 2b and the two conduits 3a and 3b, the numbers of attachment portions and conduits may also be three or more.

Endoscopes 100a and 100b are attached to the attachment portions 2a and 2b. Types of the endoscopes 100a and 100b may also be different. In the endoscope 100a, an ID chip 101a on which endoscope information such as a type and a volume of the endoscope 100a is recorded is incorporated. Similarly, in the endoscope 100b, an ID chip 101b on which endoscope information such as a type, a volume, or a use history of the endoscope 100b is recorded. It should, be noted that the ID chips 101a and 101b may also be integrally provided on outsides of the endoscopes 100a and 100b, respectively so as not to come off the endoscopes 100a and 100b.

The attachment portion 2a is connected to a distal end of the conduit 3a, and the water leakage sensing portion 4 is connected to a rear end. The conduit 3a communicates via the attachment portion 2a with an inside of the endoscope 100a attached to the attachment portion 2a. Similarly, the attachment portion 2b is connected to a distal end of the conduit 3b, and the water leakage sensing portion 4 is connected to a rear end. The conduit 3b communicates via the attachment portion 2b with an inside of the second endoscope 100b attached to the attachment portion 2b.

The water leakage sensing portion 4 communicates with the attachment portions 2a and 2b via the conduits 3a and 3b, respectively. Also, the water leakage sensing portion 4 can simultaneously carry out a plurality of items of a water leakage sensing menu for the endoscopes 100a and 100b attached to the attachment portions 2a and 2b based on control of the control portion 6.

The endoscope information reading portion 5 is, for example, an RFID antenna. The endoscope information reading portion 5 reads out endoscope information on the endoscope 100a from the ID chip 101a and outputs the read-out endoscope information on the endoscope 100a to the control portion 6. Similarly, the endoscope information reading portion 5 reads out endoscope information on the endoscope 100b from the ID chip 101b and outputs the read-out endoscope information on the endoscope 100b to the control portion 6. To deal with an endoscope without an ID chip, the endoscope information reading portion 5 may have a function to read out endoscope information by a conventionally known method other than an RFID, or a user may also manually input endoscope information.

The control portion 6 determines an item of a water leakage check menu for the endoscope 100a based on the inputted endoscope information on the endoscope 100a and assigns the determined item of the water leakage check menu to any one of the attachment portions 2a and 2b at which the item is carried out. It should be noted that in the following description, it is assumed that an item of the water leakage check menu of the endoscope 100a is assigned to the attachment portion 2a. The control portion 6 outputs to the notifying portion 7 attachment portion identifying information for identifying the assigned attachment portion 2a.

The notifying portion 7 notifies attachment portion identifying information for identifying the assigned attachment portion 2a inputted from the control portion 6. A checker attaches the endoscope 100a for water leakage sensing to the attachment portion 2a based on the attachment portion identifying information which has been notified.

Next, the control portion 6 determines an item of the water leakage check menu for the endoscope 100b based on the inputted endoscope information on the endoscope 100b and assigns the determined item of the water leakage check menu to any one of the attachment portions 2a and 2b at which the item is carried out. It should be noted that in the following description, it is assumed that an item of the water leakage check menu of the endoscope 100b is assigned to the attachment portion 2b. The control portion 6 outputs to the notifying portion 7 attachment portion identifying information for identifying the assigned attachment portion 2b to which the endoscope 100b for water leakage sensing is attached.

The notifying portion 7 notifies the attachment portion identifying information, inputted from the control portion 6, for identifying the assigned attachment portion 2b to which the endoscope 100b for water leakage sensing is attached.

The notifying portion 7 is, for example, a display that displays a name or a position of the assigned attachment portion 2a or 2b. It should be noted that the notifying portion 7 may also be a lighting portion such as an LED installed in each of the attachment portions 2a and 2b, or installed near each of the attachment portions 2a and 2b. In such a case, only a lighting portion installed in or near the assigned attachment portion 2a or 2b illuminates or blinks. Also, the notifying portion 7 may be a voice outputting portion such as a speaker that outputs a name or a position of the assigned attachment portion 2a or 2b by voice.

Next, an operation of the water leakage checking apparatus 1 having such a configuration will be described.

First, the checker turns on a power supply, not shown, of the water leakage checking apparatus 1 to cause the endoscope information reading portion 5 to read the endoscope information recorded on the ID chip 101a of the endoscope 100a in which water leakage checking is carried out. The endoscope information on the endoscope 100a read by the endoscope information reading portion 5 is supplied to the control portion 6.

Based on the supplied endoscope information, the control portion 6 determines an item of the water leakage check menu for the endoscope 100a and assigns the item of the water leakage check menu for the endoscope 100a to the attachment portion 2a. Then, attachment portion identifying information for identifying the assigned attachment portion 2a is outputted from the control portion 6 to the notifying portion 7, and the notifying portion 7 notifies the attachment portion identifying information. As a result, the checker is allowed to attach the endoscope 100a to the attachment portion 2a to which the item of the water leakage check menu for the endoscope 100a is assigned.

Next, the checker causes the endoscope information reading portion 5 to read endoscope information recorded on the ID chip 101b of the endoscope 100b in which water leakage checking is carried out. The endoscope information on the endoscope 100b read by the endoscope information reading portion 5 is supplied to the control portion 6.

Based on the supplied endoscope information, the control portion 6 determines an item of the water leakage check menu for the endoscope 100b and assigns the item of the water leakage check menu for the endoscope 100b to the attachment portion 2b. Then, attachment portion identifying information for identifying the assigned attachment portion 2b is outputted from the control portion 6 to the notifying portion 7, and the notifying portion 7 notifies the attachment portion identifying information. As a result, the checker is allowed to attach the endoscope 100b to the attachment portion 2b to which the item of the water leakage check menu for the endoscope 100b is assigned.

Thus, in the water leakage checking apparatus 1, the endoscope information reading portion 5 reads endoscope information on an endoscope in which water leakage checking is carried out, for example, the endoscope 100a, and assigns an item of the water leakage check menu to one of the attachment portions 2a and 2b, for example, the attachment portion 2a. Then, the water leakage checking apparatus 1 causes the notifying portion 7 to notify attachment portion identifying information for identifying the attachment portion 2a to which the item of the water leakage check menu is assigned. Similarly, for the endoscope 100b, the water leakage checking apparatus 1 causes the notifying portion 7 to notify attachment portion identifying information for identifying the attachment portion 2b to which an item of the water leakage check menu is assigned. As a result, the checker is allowed to easily recognize the attachment portions 2a and 2b to which the endoscopes 100a and 100b are to be attached.

Therefore, according to the water leakage checking apparatus of the present embodiment, when water leakage checking is carried out for a plurality of endoscopes, erroneous connection can be prevented.

Second Embodiment

Next, a second embodiment will be described.

Figure 2:
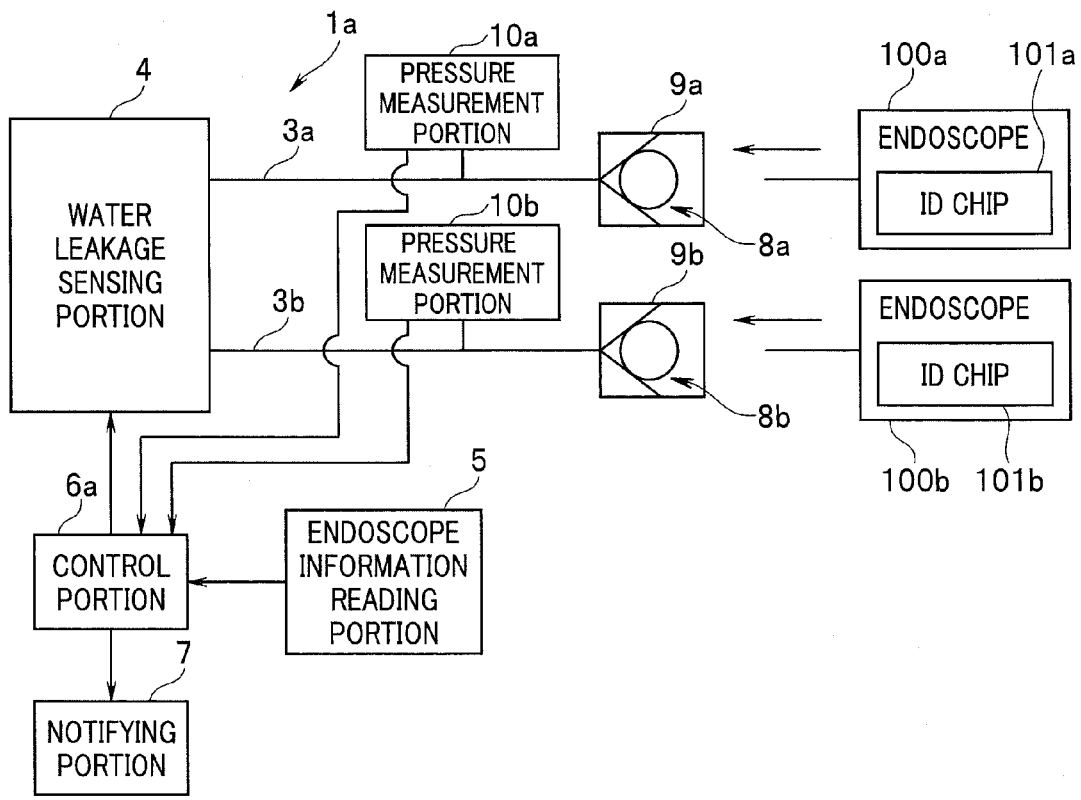
FIG. 2 is a diagram showing a configuration of a water leakage checking apparatus according to a second embodiment.

FIG. 2 is a diagram showing a configuration of a water leakage checking apparatus according to the second embodiment. It should be noted that in FIG. 2, same reference numerals are used for denoting the same components as those in FIG. 1, and descriptions thereof are omitted.

As shown in FIG. 2, a water leakage checking apparatus 1a includes a control portion 6a instead of the control portion 6 in FIG. 1. Also, in the water leakage checking apparatus 1a, an attachment portion 9a including a check valve 8a and an attachment portion 9b including a check valve 8b are provided at the distal ends of the conduits 3a and 3b, respectively. Also, in the water leakage checking apparatus 1a, pressure measurement portions 10a and 10b are provided at predetermined positions on the conduits 3a and 3b, respectively.

The check valve 8a is closed to achieve airtightness when an endoscope, for example, the endoscope 100a is not attached to the attachment portion 9a, and when the endoscope 100a is attached, the check valve 8a is opened. Similarly, the check valve 8b is closed to achieve airtightness when an endoscope, for example, the endoscope 100b is not attached to the attachment portion 9b, and when the endoscope 100b is attached, the check valve 8b is opened.

The pressure measurement portions 10a and 10b are electrically connected to the control portion 6a. The pressure measurement portions 10a and 10b measure pressures in the conduits 3a and 3b, respectively and output the measured pressure values to the control portion 6a.

In the present embodiment, if the water leakage sensing portion 4 is powered on, the water leakage sensing portion 4 supplies gas such as air to the conduits 3a and 3b through a pump, not shown, based on the control of the control portion 6a to pressurize the conduits 3a and 3b up to a predetermined pressure P. It should be noted that the process for pressurizing up to the predetermined pressure P may also be carried out after endoscope information is read by the endoscope information reading portion 5. The control portion 6a detects whether or not the pressures in the conduits 3a and 3b have reached the predetermined pressure P based on the pressure values in the conduits 3a and 3b inputted from the pressure measurement portions 10a and 10b. When the control portion 6a detects that the pressures in the conduits 3a and 3b have reached the predetermined pressure P, the control portion 6a stops the supply of gas from the water leakage sensing portion 4.

If the endoscope 100a is attached to the attachment portion 9a to which an item of the water leakage sensing menu for the endoscope 100a is assigned, the conduit 3a and a conduit in the endoscope 100a are communicated with each other, and the pressure in the conduit 3a is lowered. The lowered pressure value in the conduit 3a is outputted from the pressure measurement portion 10a to the control portion 6a.

The control portion 6a senses that the endoscope 100a is correctly connected to the attachment portion 9a by detecting the lowered pressure value in the conduit 3a. If the control portion 6a senses the correct connection, the control portion 6a outputs to the notifying portion 7 information indicating that the endoscope 100a is correctly connected to the attachment portion 9a and causes the notifying portion 7 to notify the information.

If the endoscope 100a is attached to the attachment portion 9b, to which an item of the water leakage sensing menu for the endoscope 100a is not assigned, the conduit 3b and the conduit in the endoscope 100a are communicated with each other, and the pressure in the conduit 3b is lowered. The lowered pressure value in the conduit 3b is outputted from the pressure measurement portion 10b to the control portion 6a.

The control portion 6a senses that the endoscope 100a is erroneously connected to the attachment portion 9b, to which an item of the water leakage sensing menu for the endoscope 100a is not assigned, by detecting the lowered pressure value in the conduit 3b. If the control portion 6a senses the erroneous connection, the control portion 6a outputs to the notifying portion 7 error information indicating that the endoscope 100a is not attached to the attachment portion 9a correctly and causes the notifying portion 7 to notify the information.

Next, an operation of the water leakage checking apparatus 1a having such a configuration will be described.

First, once the checker turns on a power supply, not shown, of the water leakage checking apparatus 1a, the conduits 3a and 3b are pressurized up to the predetermined pressure P. Next, the checker causes the endoscope information reading portion 5 to read the endoscope information recorded on the ID chip 101a of the endoscope 100a in which the water leakage checking is carried out. Thereby, an item of the water leakage check menu for the endoscope 100a is assigned to the attachment portion 9a and attachment portion identifying information for identifying the assigned attachment portion 9a is outputted from the control portion 6a to the notifying portion 7. Then, the notifying portion 7 notifies the attachment portion identifying information.

If the checker correctly attaches the endoscope 100a to the attachment portion 9a based on the attachment portion identifying information notified by the notifying portion 7, the conduit 3a and the conduit of the endoscope 100a are communicated with each other, and the conduit 3a is decompressed. This pressure change is outputted from the pressure measurement portion 10a provided on the conduit 3a to the control portion 6a and the correct attachment of the endoscope 100a to the attachment portion 9a is recognized. Thus, based on the control of the control portion 6a, the notifying portion 7 notifies information indicating the correct attachment.

If the checker connects the endoscope 100a to the attachment portion 9b erroneously, the conduit 3b and the conduit of the endoscope 100a are communicated with each other, and the conduit 3b is decompressed. This pressure change is outputted from the pressure measurement portion 10b provided on the conduit 3b to the control portion 6a and it is recognized that the endoscope 100a is not correctly attached to the attachment portion 9a. That is, although the control portion 6a has instructed the checker to attach the endoscope 100a to the attachment portion 9a, since the pressure of the conduit 3b connected to the attachment portion 9b, not the pressure of the conduit 3a connected to the attachment portion 9a, is lowered, it is determined that the endoscope 100a is not correctly attached to the attachment portion 9a. Thus, based on the control of the control portion 6a, the notifying portion 7 notifies error information indicating the incorrect attachment.

As hereinbefore described, since the water leakage checking apparatus 1a can automatically determine whether the two endoscopes 100a and 100b are correctly attached to the assigned attachment portions 9a and 9b, water leakage checking in an erroneous connection state can be prevented. Also, if the water leakage checking apparatus 1a senses an erroneous connection, since the notifying portion 7 notifies error information, the checker can easily find the erroneous connection.

Modification 1 of Second Embodiment

As a modification of the second embodiment, there may be a constitution including one openable/closable valve between the pressure measurement portion 10a and the water leakage sensing portion 4, and another between the pressure measurement portion 10b and the water leakage sensing portion 4. Further, it is desirable that the control portion 6a be able to control the valves.

The pressure in each of the conduits 3a and 3b pressurized by the pump can be maintained in a predetermined pressurized state by closing each of the check valves 8a and 8b.

As an example of a use of the valves, since the supply of gas from the water leakage sensing portion can be stopped by closing the valve, when the pressure measurement portions 10a and 10b detect that the pressures in the conduits 3a and 3b reach the predetermined pressure P and the control portion 6a receives a signal of the fact, the control portion 6a may send a signal to close each valve, thereby stopping the supply of gas from the water leakage sensing portion 4.

Modification 2 of Second Embodiment

As another modification of the second embodiment, there may be connection sensing that uses the pressure measurement portions 10a and 10b. A pressure determining portion which can determine whether the pressure in the conduit 3a or 3b reaches a predetermined pressure is provided at a side of the pressure measurement portions 10a and 10b or at a side of the control portion 6a, and thereby an abnormality of the valves, the check valves 8a and 8b, or the conduits 3a and 3b as well as a connection abnormality between the check valves 8a, 8b and the endoscopes 100a, 100b can be sensed.

Specifically, the pressure determining portion is configured to be able to compare a normal pressure with pressures measured by the pressure measurement portions 10a and 10b, and if the pressure created when the valves and the check valves 8a, 8b are closed is lower than the normal pressure within a predetermined range, a gas leak due to a failure of the valves, the check valves 8a, 8b, or the conduits 3a, 3b can be sensed. Also, a gas leak due to improper engagement of the check valves 8a, 8b with the endoscopes 100a, 100b can be sensed.

If such an abnormality is sensed, the notifying portion 7 may also be used to notify the abnormality.

Third Embodiment

Next, a third embodiment will be described.

Figure 3:
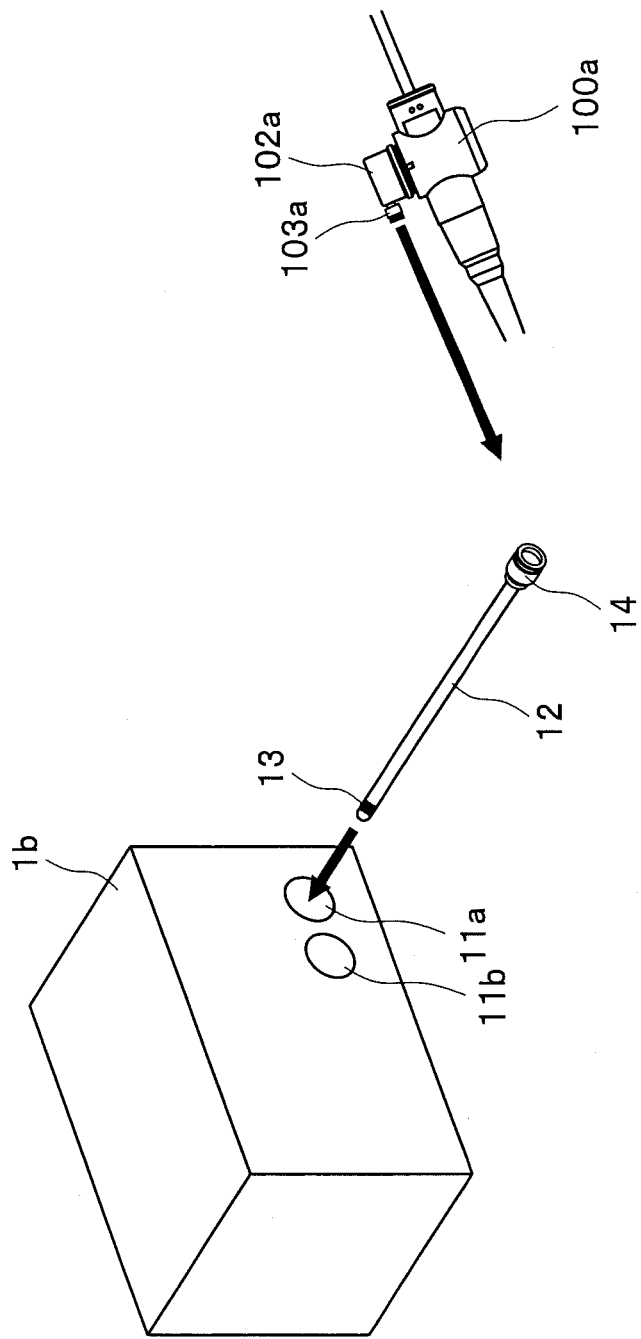
FIG. 3 is a diagram showing a configuration of a water leakage checking apparatus according to a third embodiment.

FIG. 3 is a diagram showing a configuration of a water leakage checking apparatus according to the third embodiment. It should be noted that in FIG. 3, same reference numerals are used for denoting the same components as those in FIG. 2, and descriptions thereof are omitted.

As shown in FIG. 3, a water leakage checking apparatus 1b includes a plurality of, here, two connection ports 11a and 11b for connecting a tube 12 used to connect the endoscope 100a with the water leakage checking apparatus 1b. It should be noted that since the connection ports 11a and 11b have the same configuration, hereinafter, only the connection port 11a will be described. One end of the tube 12 is provided with a connection pipe sleeve 13 to be connected with the water leakage checking apparatus 1b. Also, the other end of the tube 12 is provided with an endoscope pipe sleeve 14 to be connected with a waterproof pipe sleeve 103a of a waterproof cap 102a covering the endoscope 100a or an electrical connector of the endoscope 100a.

Figure 4:
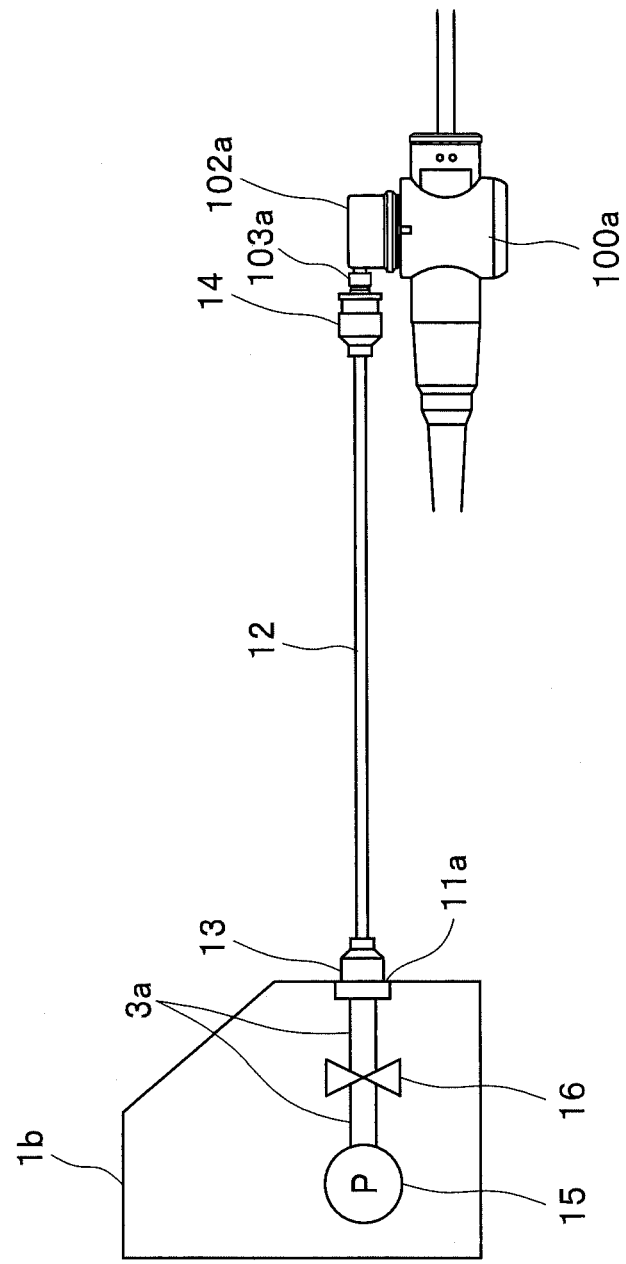
FIG. 4 is a diagram for illustrating an internal configuration of the water leakage checking apparatus according to the third embodiment.

FIG. 4 is a diagram for illustrating an internal configuration of the water leakage checking apparatus according to the third embodiment.

As shown in FIG. 4, in the water leakage checking apparatus 1b, a rear end of the connection port 11a is connected with the conduit 3a, and a rear end of the conduit 3a is connected with a pump 15. Also, a cutoff valve 16 is provided midway along the conduit 3a.

In such a configuration, if the connection pipe sleeve 13 of the tube 12 is connected with the connection port 11a, and the endoscope pipe sleeve 14 is connected with the waterproof pipe sleeve 103a, the conduit 3a from the cutoff valve 16 to the connection port 11a, the inside of the tube 12, and an airtight area of the endoscope 100a are connected to each other, and they are maintained airtight.

Now, a detailed configuration of the connection port and the connection pipe sleeve will be described with reference to FIG. 5 and FIG. 6.

Figure 5:
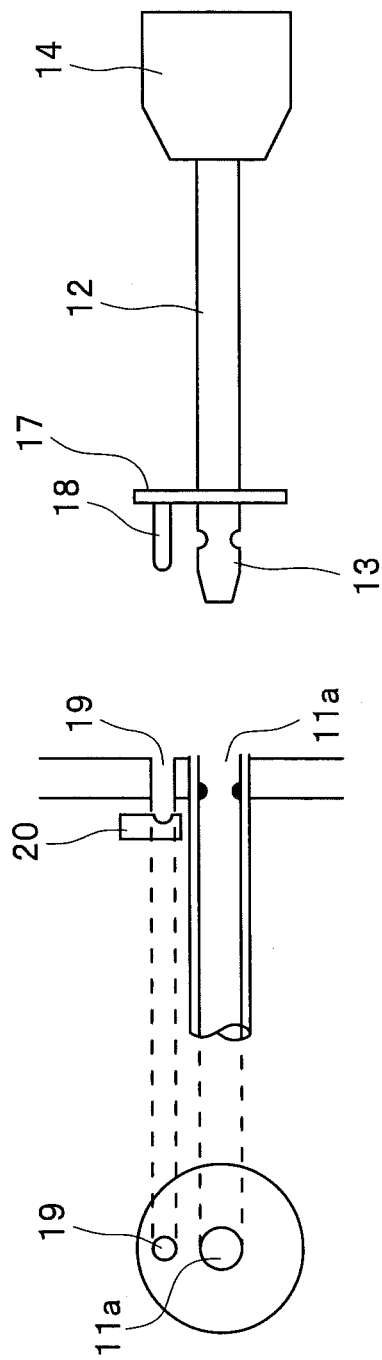
FIG. 5 is a diagram for illustrating a detailed configuration of a connection port and a connection pipe sleeve.
Figure 6:
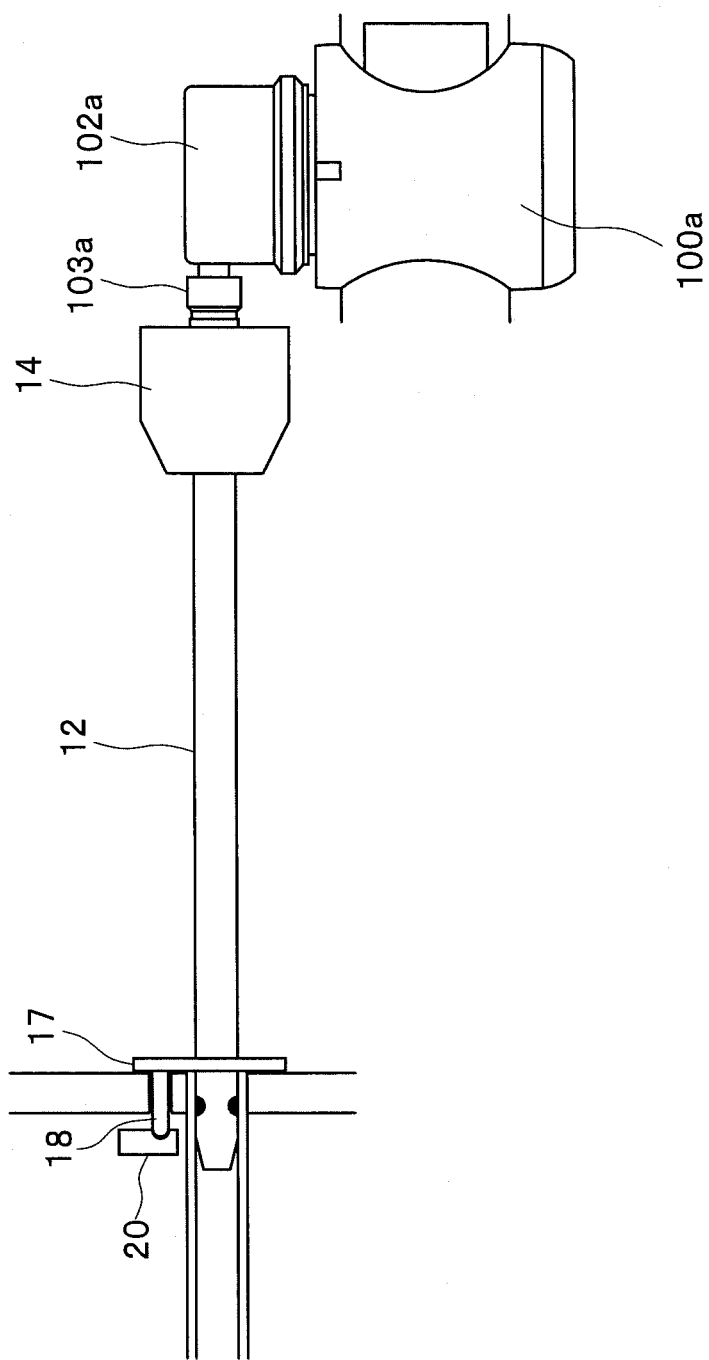
FIG. 6 is a diagram for illustrating a condition where the connection port and the connection pipe sleeve are connected with each other.

FIG. 5 is a diagram for illustrating the detailed configuration of the connection port and the connection pipe sleeve, and FIG. 6 is a diagram for illustrating a condition where the connection port and the connection pipe sleeve are connected with each other.

As shown in FIG. 5, a flange 17 is provided near the connection pipe sleeve 13 of the tube 12. At a predetermined position on the flange 17, a protrusion portion 18 pointing to the water leakage checking apparatus 1b is provided in parallel with a longitudinal axis direction of the tube 12.

On the other hand, a protrusion portion insertion opening 19 is provided above the connection port 11a of the water leakage checking apparatus 1b, and the opening 19 is shaped so that the protrusion portion 18 is inserted therein when the connection pipe sleeve 13 is connected to the connection port 11a. On a rear side of the protrusion portion insertion opening 19, a press button switch 20 is provided at a position which the protrusion portion 18 can push as shown in FIG. 6 when the connection pipe sleeve 13 is connected with the connection port 11a so as to achieve airtightness.

The press button switch 20 is electrically connected to the control portion 6a and outputs a depression sensed signal indicating whether the press button switch 20 is depressed by the protrusion portion 18 to the control portion 6a. Thereby, the control portion 6a determines whether or not the endoscope 100a is correctly connected with the connection port 11a and causes the notifying portion 7 to notify a determination result.

It should be noted that the configuration for sensing the connection between the connection port 11a and the connection pipe sleeve 13 is not limited to the configuration of the protrusion portion 18 and the press button switch 20. For example, there may be a configuration for sensing connection by a protrusion portion blocking an optical axis of an optical sensor, a configuration for sensing connection by a metal protrusion portion and a metal sensor, a configuration for sensing connection by a magnetized metal protrusion portion and a magnetic sensor, and a configuration for sensing connection by an RFID antenna reading an RFID chip incorporated in a protrusion portion. In such a configuration, since there is no mechanical connection during the sensing, durability of the water leakage checking apparatus 1b is allowed to be improved.

Next, an operation of the water leakage checking apparatus 1b having such a configuration will be described.

First, the checker turns on a power supply, not shown, of the water leakage checking apparatus 1b and allows the endoscope information reading portion 5 to read endoscope information recorded on the ID chip 101a of the endoscope 100a in which the water leakage checking is carried out. In response, an item of the water leakage check menu for the endoscope 100a is assigned to the connection port 11a. Next, the checker connects the endoscope pipe sleeve 14 to the waterproof pipe sleeve 103a and the connection pipe sleeve 13 to the assigned connection port 11a.

If the connection pipe sleeve 13 is connected with the connection port 11a, the press button switch 20 is depressed by the protrusion portion 18. A depression sensed signal is outputted from the press button switch 20 to the control portion 6a, and the control portion 6a determines whether or not the endoscope 100a is correctly connected. The notifying portion 7 notifies a determination result as to whether the endoscope 100a has been correctly connected. Because the other operations are similar to those in the second embodiment, a description thereof will be omitted.

As hereinbefore described, the water leakage checking apparatus 1b automatically recognizes whether the water leakage checking apparatus 1b and the tube 12 has been correctly connected to each other in response to a depression sensed signal from the press button switch 20, and notifies a result thereof. Therefore, erroneous connecting made by the checker can be reliably prevented.

Figure 7:
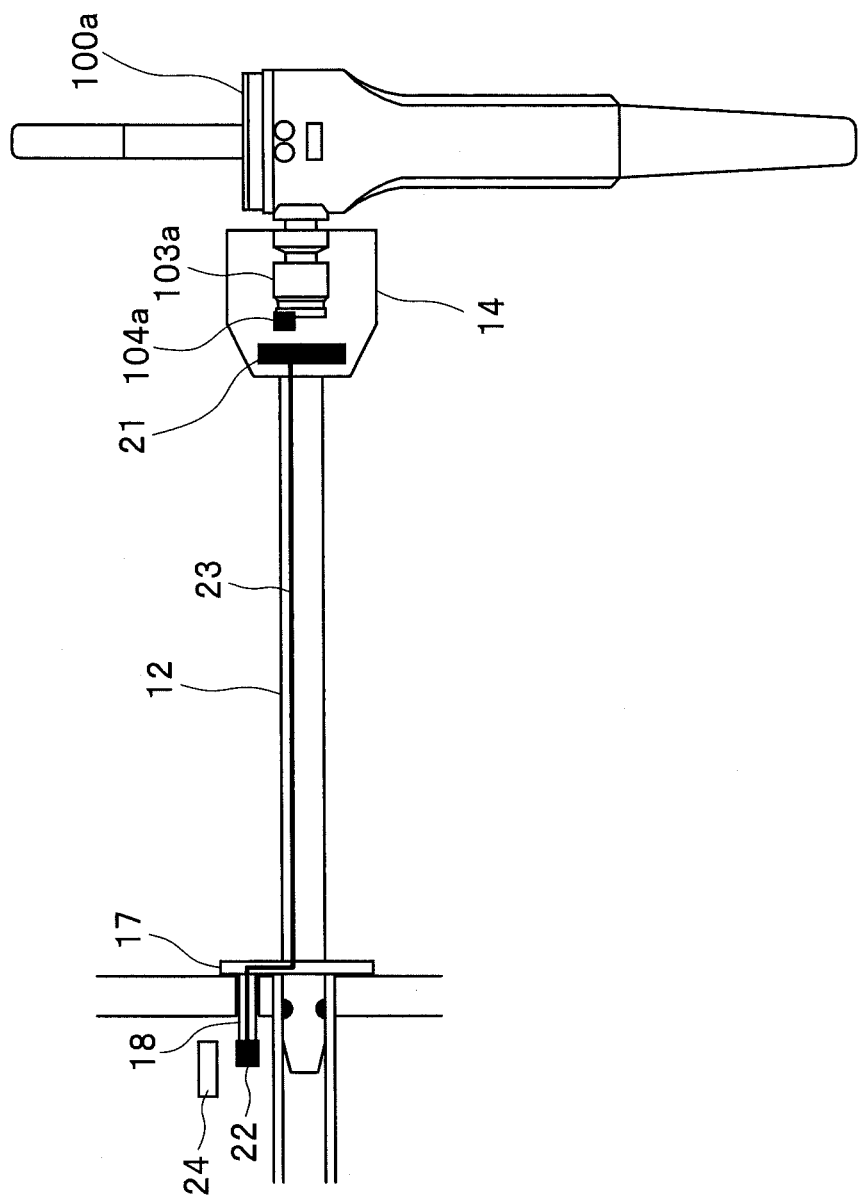
FIG. 7 is a diagram for illustrating connection of the water leakage checking apparatus, a tube, and an endoscope.

Meanwhile, as a configuration for sensing that the water leakage checking apparatus 1b, the tube 12, and the endoscope 100a are reliably connected with each other, there may be a configuration as shown in FIG. 7.

FIG. 7 is a diagram for illustrating connection of the water leakage checking apparatus, the tube, and the endoscope.

As shown in FIG. 7, the endoscope 100a includes an ID chip 104a on which endoscope information is recorded near a distal end portion of the waterproof pipe sleeve 103a.

In the endoscope pipe sleeve 14 of the tube 12, an RFID antenna 21 is provided to, when the endoscope pipe sleeve 14 is connected with the waterproof pipe sleeve 103a, come close enough to read the endoscope information from the ID chip 104a. Also, a distal end of the protrusion portion 18 of the tube 12 is provided with an ID chip 22.

The RFID antenna 21 and the ID chip 22 are connected to each other via a communication cable 23 inserted in the tube 12, the flange 17, and the protrusion portion 18. The RFID antenna 21 can transmit the endoscope information read out from the ID chip 104a to the ID chip 22 through the communication cable 23.

In the water leakage checking apparatus 1b, an RFID antenna 24 is provided to, when the connection pipe sleeve 13 of the tube 12 is connected to the connection port 11a, come close enough to read the endoscope information transmitted to the ID chip 22. The RFID antenna 24 reads out the endoscope information transmitted from the RFID antenna 21 to the ID chip 22, and outputs the endoscope information to the control portion 6a.

According to such a configuration, when the endoscope pipe sleeve 14 and the waterproof pipe sleeve 103a are connected with each other, the RFID antenna 21 reads out the endoscope information recorded on the ID chip 104a and transmits the read-out endoscope information to the ID chip 22. Also, when the connection pipe sleeve 13 and the connection port 11a are connected with each other, the RFID antenna 24 reads out the endoscope information transmitted to the ID chip 22 and outputs the read-out endoscope information to the control portion 6a. As a result, the configuration can sense that the tube 12 is correctly connected with the water leakage checking apparatus 1b and the endoscope 100a. Also, if the correct connection is achieved, since the endoscope information on the endoscope 100a is automatically read out to the water leakage checking apparatus 1b, it is not necessary for the checker to cause the endoscope information reading portion 5 to read the endoscope information.

Fourth Embodiment

Next, a fourth embodiment will be described.

Figure 8:
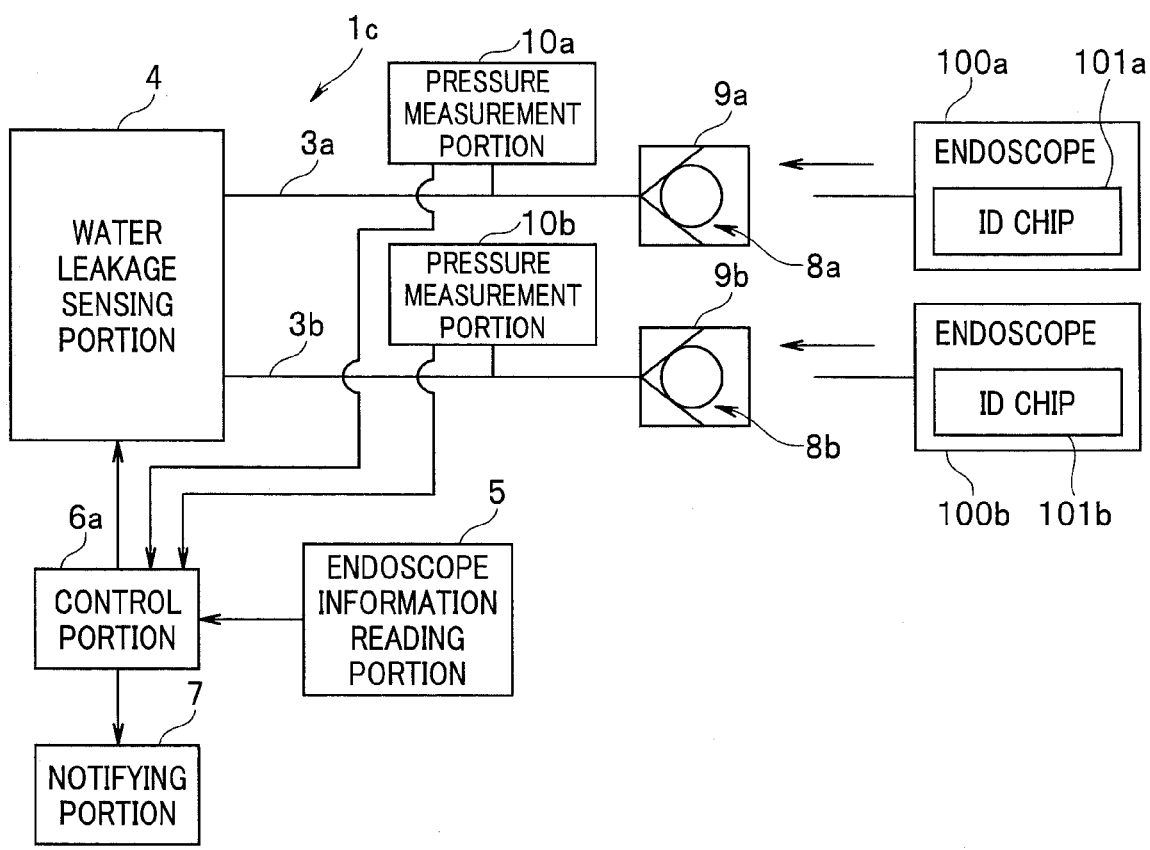
FIG. 8 is a diagram showing a configuration of a water leakage checking apparatus according to a fourth embodiment.

FIG. 8 is a diagram showing a configuration of a water leakage checking apparatus according to the fourth embodiment. It should be noted that in FIG. 8, same reference numerals are used for denoting the same components as those in FIG. 2, and descriptions thereof are omitted.

As shown in FIG. 8, a water leakage checking apparatus 1c includes a control portion 6b instead of the control portion 6a in FIG. 2.

Once a power supply is turned on, the control portion 6b instructs the water leakage sensing portion 4 to pressurize only any one of the conduits 3a and 3b up to the predetermined pressure P. Here, it is assumed that the control portion 6b instructs the water leakage sensing portion 4 to pressurize the conduit 3a. Then, when the control portion 6b reads out the endoscope information recorded on the ID chip 101a, the control portion 6b assigns an item of the water leakage check menu for the endoscope 100a to the attachment portion 9a.

When the endoscope 100a is attached to the attachment portion 9a, the control portion 6b senses a pressure change from the pressure measurement portion 10a and recognizes that the correct connection has been achieved. If the control portion 6b recognizes that the correct connection has been achieved, the control portion 6b causes the water leakage sensing portion 4 to carry out the item of the water leakage check menu assigned to the attachment portion 9a.

In contrast, if the endoscope 100a is attached to the attachment portion 9b, since the conduit 3b is not pressurized, the control portion 6b does not sense a pressure change from the pressure measurement portion 10b. The control portion 6b determines that the correct connection is not achieved for a period during which a pressure change is not sensed, and does not cause the water leakage sensing portion 4 to carry out the item of the water leakage check menu.

Next, an operation of the water leakage checking apparatus 1c having such a configuration will be described.

First, when the checker turns on a power supply, not shown, of the water leakage checking apparatus 1c, any one of the conduits 3a and 3b, here, the conduit 3a is pressurized to the predetermined pressure P. Then, the checker allows the endoscope information reading portion 5 to read endoscope information recorded on the ID chip 101a of the endoscope 100a in which the water leakage checking is carried out. In response, an item of the water leakage check menu for the endoscope 100a is assigned to the attachment portion 9a. Then, attachment portion identifying information for identifying the assigned attachment portion 9a is outputted from the control portion 6b to the notifying portion 7, and the notifying portion 7 notifies the attachment portion identifying information.

Once the checker attaches the endoscope 100a to the assigned attachment portion 9a, the conduit 3a connected with the attachment portion 9a is decompressed, and information about the pressure change is outputted from the pressure measurement portion 10a to the control portion 6b. The control portion 6b recognizes that the endoscope 100a is correctly attached to the attachment portion 9a based on the information about the pressure change, and causes the water leakage sensing portion 4 to carry out the item of the water leakage check menu. In contrast, if pressure change information is not received (as input), the control portion 6b determines that the endoscope 100a is not correctly attached to the attachment portion 9a and does not cause the water leakage sensing portion 4 to carry out the item of the water leakage check menu.

As hereinbefore described, if the endoscope 100a is not correctly attached to the attachment portion 9a, since the water leakage checking apparatus 1c does not cause an item of the water leakage check menu to be carried out, an item of the water leakage check menu can be prevented from being carried out in an erroneous connection state. Also, the checker is allowed to easily recognize erroneous connection because the water leakage check menu is not carried out in an erroneous connection state.

Fifth Embodiment

Next, a fifth embodiment will be described.

Figure 10A:
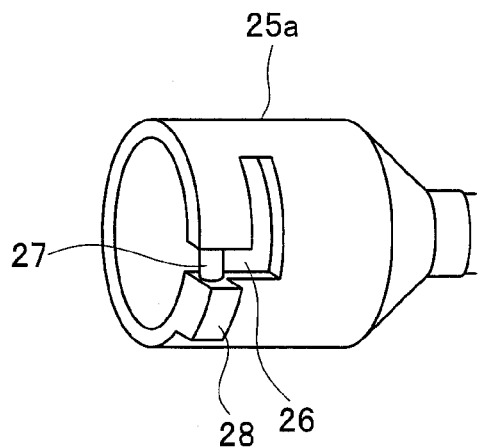
FIG. 10A is a diagram for illustrating a detailed configuration of an attachment portion in a closed condition.
Figure 10B:
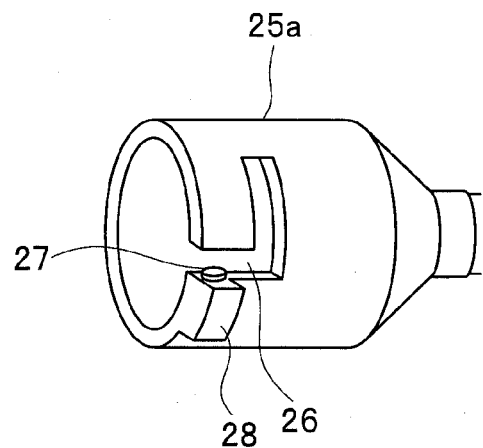
FIG. 10B is a diagram for illustrating a detailed configuration of the attachment portion in the opened condition.
Figure 11A:
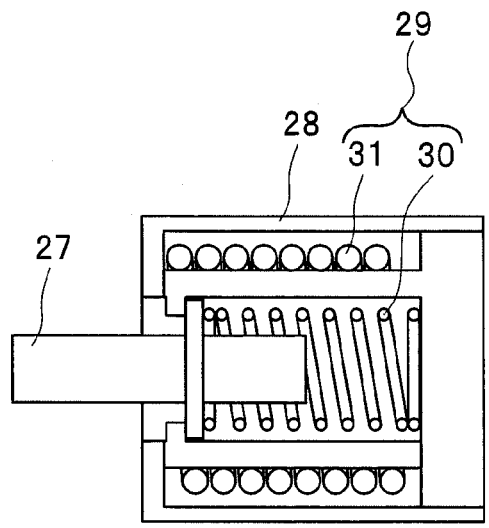
FIG. 11A is a cross-sectional view for illustrating a configuration of a solenoid housing portion in the closed condition.
Figure 11B:
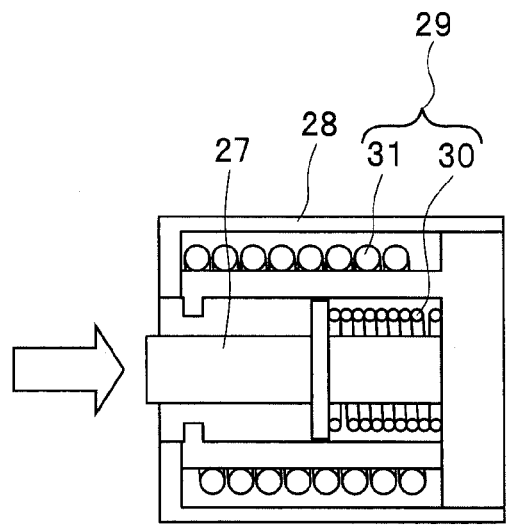
FIG. 11B is a cross-sectional view for illustrating a configuration of the solenoid housing portion in an opened condition.

FIG. 9 is a diagram showing a configuration of a water leakage checking apparatus according to the fifth embodiment, FIG. 10A is a diagram for illustrating a detailed configuration of an attachment portion in a closed condition, FIG. 10B is a diagram for illustrating a detailed configuration of the attachment portion in an opened condition, FIG. 11A is a cross-sectional view for illustrating a configuration of a solenoid housing portion in the closed condition, and FIG. 11B is a cross-sectional view for illustrating a configuration of the solenoid housing portion in the opened condition. It should be noted that in FIG. 9, same reference numerals are used for denoting the same components as those in FIG. 8, and descriptions thereof are omitted.

As shown in FIG. 9, a water leakage checking apparatus 1d includes a control portion 6c, an attachment portion 25a, and an attachment portion 25b instead of the control portion 6b, the attachment portion 9a, and the attachment portion 9b in FIG. 8. The attachment portions 25a and 25b are electrically connected with the control portion 6c.

As shown in FIG. 10A, a notch portion 26 is provided at the attachment portion 25a, and a pin 105a (see FIG. 9) provided on the waterproof pipe sleeve 103a of the endoscope 100a is fitted in the notch portion 26. Also, a solenoid housing portion 28 in which a solenoid 29 for moving a movable core 27 is housed is provided at the attachment portion 25a.

As shown in FIG. 11A, the solenoid 29 includes a spring 30 urging the movable core 27 and a coil 31 around the spring 30. If the coil 31 is not energized, an urging force of the spring 30 pushes out the movable core 27 to a distal end side, and as shown in FIG. 10A, the notch portion 26 is closed by the movable core 27.

In contrast, if the coil 31 is energized by the control of the control portion 6c, a magnetic force is generated, and as shown in FIG. 11B, the movable core 27 is retreated against the urging force of the spring 30 in a rear end side. Then, as shown in FIG. 10B, the notch portion 26 is opened. As such, the movable core 27 is an opening/closing portion that closes or opens the notch portion 26.

If an item of the water leakage sensing menu for the endoscope 100a is assigned to the attachment portion 25a, the control portion 6c gives an instruction to open the notch portion 26 of the attachment portion 25a, that is, to energize the coil 31. In response, the control portion 6c opens the notch portion 26 of the attachment portion 25a. If the control portion 6c senses that the endoscope 100a is attached to the attachment portion 25a based on a pressure change from the pressure measurement portion 10a, the control portion 6c gives an instruction to de-energize the coil 31. In response, the control portion 6c closes the notch portion 26 of the attachment portion 25a by the movable core 27.

Next, an operation of the water leakage checking apparatus 1d having such a configuration will be described.

First, once the checker turns on a power supply, not shown, of the water leakage checking apparatus 1d, the conduits 3a and 3b are pressurized to the predetermined pressure P, and the pressure is maintained. The control portion 6c recognizes the pressure-maintained condition, instructs the notifying portion 7 to notify a message "Please let the endoscope information reading portion 5 read the ID chip," and causes the notifying portion 7 to carry out the notification. Then, the checker causes the endoscope information reading portion 5 to read the endoscope information recorded in the ID chip 101a of the endoscope 100a. The control portion 6c assigns an item of the water leakage check menu to one of the attachment portions 25a and 25b, in this example, to the attachment portion 25a.

The control portion 6c gives an instruction to open the notch portion 26 for the assigned attachment portion 25a. In response to the instruction from the control portion 6c, the coil 31 of the solenoid 29 of the attachment portion 25a is energized and the movable core 27 moves. As a result, the notch portion 26 of the attachment portion 25a is opened and the checker is allowed to attach the waterproof pipe sleeve 103a of the endoscope 100a to the attachment portion 25a.

If the endoscope 100a is connected with the attachment portion 25a in which the notch portion 26 is opened, since the conduit in the endoscope 100a communicates with a conduit in the attachment portion 25a, a pressure value in the conduit 3a is lowered. If the pressure change is sensed by the control portion 6c, the control portion 6c recognizes that the endoscope 100a is attached to the attachment portion 25a and gives an instruction to the attachment portion 25a to de-energize the coil.

In response to the instruction from the control portion 6c, the coil 31 in the solenoid 29 is de-energized. As a result, the movable core 27 is pushed back by the force of the spring 30 of the solenoid 29, and thereby the notch portion 26 of the attachment portion 25a is closed. Thus, the waterproof pipe sleeve 103a of the endoscope 100a becomes unable to be detached from the attachment portion 25a. The checker repeats the foregoing operation for the endoscope 100b, thereby attaching the endoscope 100b to the attachment portion 25b.

When the control portion 6c recognizes that the two endoscopes 100a and 100b are attached to the attachment portions 25a and 25b, respectively, the control portion 6c instructs the water leakage sensing portion 4 to carry out water leakage checking depending on types of the endoscopes 100a and 100b, and allows the water leakage sensing portion 4 to carry out the water leakage checking. Simultaneously, the control portion 6c instructs the notifying portion 7 to notify a message "Now water leakage is being checked," and causes the notifying portion 7 to carry out the notification.

If the water leakage checking is completed, the control portion 6c instructs the notifying portion 7 to notify a result of the water leakage checking, and causes the notifying portion 7 to carry out the notification. Simultaneously, the control portion 6c instructs the water leakage sensing portion 4 to decompress the conduits 3a and 3b and allows the water leakage sensing portion 4 to carry out the decompression. As a result, the pressures in the conduits 3a and 3b become equal to an atmospheric pressure.

The control portion 6c recognizes that each of the conduits 3a and 3b has been decompressed based on pressure values from the pressure measurement portions 10a and 10b and instructs the attachment portions 25a and 25b to open the notch portion 26. The checker detaches the endoscopes 100a and 100b from the attachment portions 25a and 25b and terminates the water leakage checking.

As hereinbefore described, the water leakage checking apparatus 1d opens/closes the notch portion 26 of each of the attachment portions 25a and 25b at a proper timing to physically interrupt the connection with the endoscopes 100a and 100b, and thereby erroneous connecting can be reliably prevented. As a result, even a checker who does not have a detailed knowledge of an operation method of the water leakage checking apparatus 1d can simply utilize the water leakage checking apparatus 1d.

Sixth Embodiment

Next, a sixth embodiment will be described.

Figure 12:
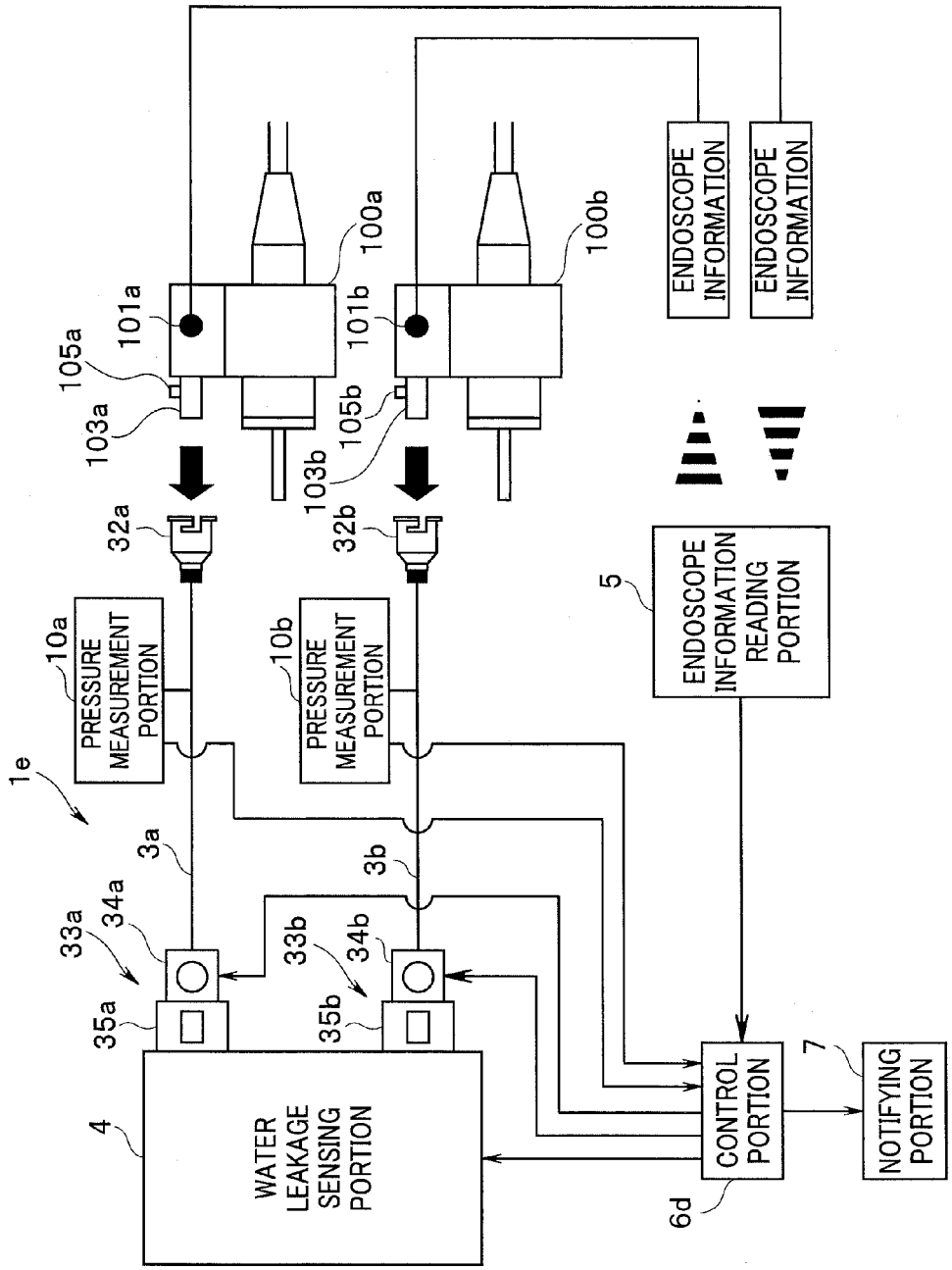
FIG. 12 is a diagram showing a configuration of a water leakage checking apparatus according to a sixth embodiment.
Figure 13:
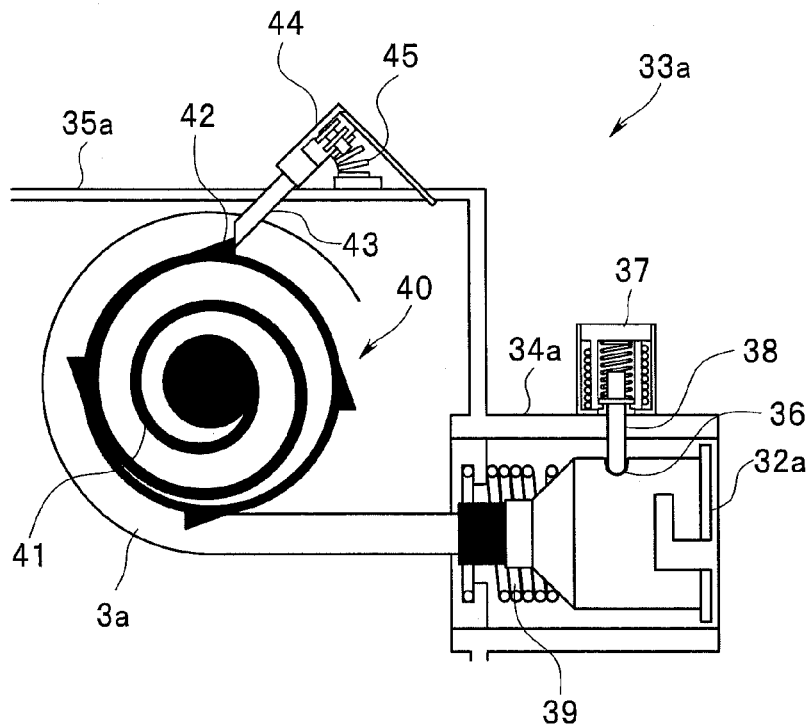
FIG. 13 is a diagram for illustrating a detailed configuration of a housing portion in which an attachment portion is housed.
Figure 14:
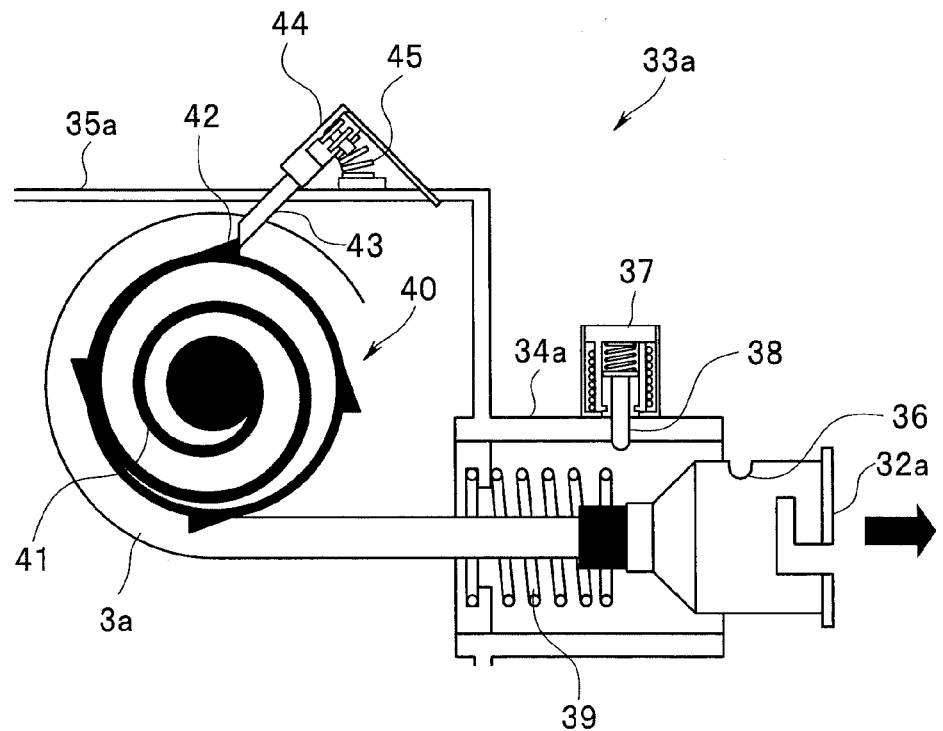
FIG. 14 is a diagram for illustrating a detailed configuration of the housing portion from which the attachment portion is taken out.
Figure 15:
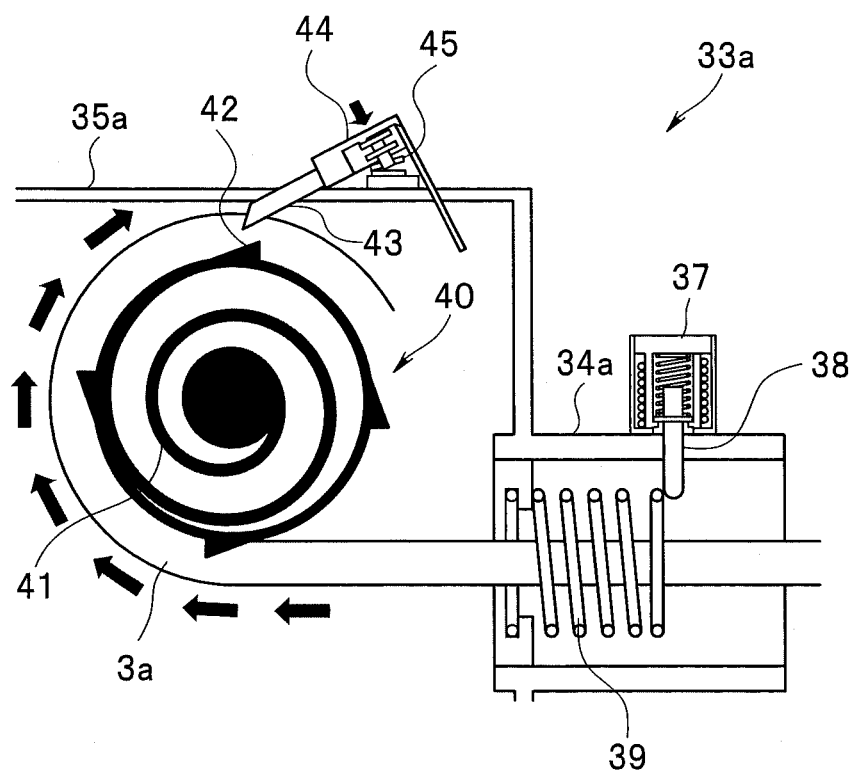
FIG. 15 is a diagram for illustrating a detailed configuration of the housing portion in which a conduit is wound.

FIG. 12 is a diagram showing a configuration of a water leakage checking apparatus according to the sixth embodiment, FIG. 13 is a diagram for illustrating a detailed configuration of a housing portion in which an attachment portion is housed, FIG. 14 is a diagram for illustrating a detailed configuration of the housing portion from which the attachment portion is taken out, and FIG. 15 is a diagram for illustrating a detailed configuration of the housing portion in which a conduit is wound. It should be noted that in FIG. 12, same reference numerals are used for denoting the same components as those in FIG. 9, and descriptions thereof are omitted.

As shown in FIG. 12, a water leakage checking apparatus 1e includes a control portion 6d, an attachment portion 32a, and an attachment portion 32b instead of the control portion 6c, the attachment portion 25a, and the attachment portion 25b in FIG. 9, respectively. Also, the water leakage sensing portion 4 includes a housing portion 33a in which the conduit 3a and the attachment portion 32a are housed and a housing portion 33b in which the conduit 3b and the attachment portion 32b are housed.

In the attachment portion 32a, the movable core 27, the solenoid housing portion 28, and the solenoid 29 are removed from the attachment portion 25a in FIG. 9. Also, as shown in FIG. 13, a notch portion 36 corresponding to a distal end shape of a movable core 38 is provided on an outer surface of the attachment portion 32a.

The housing portion 33a includes a distal end side housing portion 34a in which the attachment portion 32a is housed and a rear end side housing portion 35a in which the conduit 3a is housed. Similarly, the housing portion 33b includes a distal end side housing portion 34b in which the attachment portion 32b is housed and a rear end side housing portion 35b in which the conduit 3b is housed. It should be noted that because the housing portion 33a and the housing portion 33b have the same configuration, hereinafter, the housing portion 33a will be described.

As shown in FIG. 13, a solenoid 37 operated in response to an instruction from the control portion 6d is installed on a top surface of the distal end side housing portion 34a. When an internal coil is not energized in accordance with an instruction from the control portion 6d a distal end of the solenoid 37 pushes out the movable core 38 downward by an urging force of a spring provided therein. In contrast, when the internal coil is energized in accordance with an instruction from the control portion 6d, the solenoid 37 draws in the movable core 38 upward by a magnetic field generated by the coil.

Also, in the distal end side housing portion 34a, a spring 39 exerting an urging force when the attachment portion 32a is housed is provided. As shown in FIG. 14, once the coil of the solenoid 37 is energized and the movable core 38 is detached from the notch portion 36, the attachment portion 32a is pushed forward from the housing portion 33a by an urging force of the spring 39.

Also, in the rear end side housing portion 35a, a winding portion 40 for winding the conduit 3a is provided. The winding portion 40 includes a winding spring 41 and claw-shaped protrusion portions 42. The attachment portion 32a and the conduit 3a are drawn out, and thereby tension is generated in the winding spring 41.

In order not to wind the conduit 3a by the tension of the winding spring 41, a stopper 43 is installed to be hooked by any of the protrusion portions 42. The stopper 43 is pushed against the winding portion 40 by an urging force of a spring 45 attached to a stopper release button 44 installed on a top surface of the rear end side housing portion 35a.

As shown in FIG. 15, when the stopper release button 44 is pressed, the stopper 43 comes off the protrusion portion 42 and the winding portion 40 is allowed to automatically wind the conduit 3a by the tension generated in the winding spring 41.

Next, an operation of the water leakage checking apparatus 1e having such a configuration will be described.

First, once the checker turns on a power supply, not shown, of the water leakage checking apparatus 1e, the conduits 3a and 3b are pressurized to the predetermined pressure P. Then, the checker allows the endoscope information reading portion 5 to read endoscope information recorded on the ID chip 101a of the endoscope 100a in which the water leakage checking is carried out.

The control portion 6d recognizes the endoscope information from the endoscope information reading portion 5 and gives an instruction to energize the coil of the solenoid 37 installed in the housing portion 33a in which the attachment portion 32a is housed. In response to an instruction from the control portion 6d, the coil of the solenoid 37 is energized and the movable core 38 of the solenoid 37 moves upward, thereby coming off the notch portion 36 formed on an outer surface of the attachment portion 32a. At this time, by an urging force of the spring 39 installed at a rear end side of the attachment portion 32a, the attachment portion 32a is pushed out of the housing portion 33a.

The checker connects the endoscope 100a with the pushed-out attachment portion 32a. At this time, since the inside of the endoscope 100a communicates with the conduit in the attachment portion 32a, a pressure value in the conduit 3a is lowered.

The control portion 6d recognizes that the endoscope 100a is connected with the attachment portion 32a based on the lowered pressure value and de-energizes the solenoid 37 installed in the housing portion 33a. The checker repeats the same operation for the unconnected endoscope 100b. Then, the checker attaches the endoscopes 100a and 100b to the attachment portion 32a and 32b, respectively and carries out the water leakage checking similarly as in the fifth embodiment.

As hereinbefore described, the water leakage checking apparatus 1e is configured to read endoscope information and push out the attachable attachment portion 32a or 32b from the housing portion 33a or 33b. As a result, in the water leakage checking apparatus 1e, since the checker is allowed to visually check the attachable attachment portion 32a or 32b, erroneous connecting can be reliably prevented.

Also, in the water leakage checking apparatus 1e, the conduits 3a and 3b, and the attachment portions 32a and 32b are allowed to be housed in the water leakage sensing portion 4, so that space saving can be achieved compared with the water leakage checking apparatus 1d according to the fifth embodiment.

Seventh Embodiment

Figure 16:
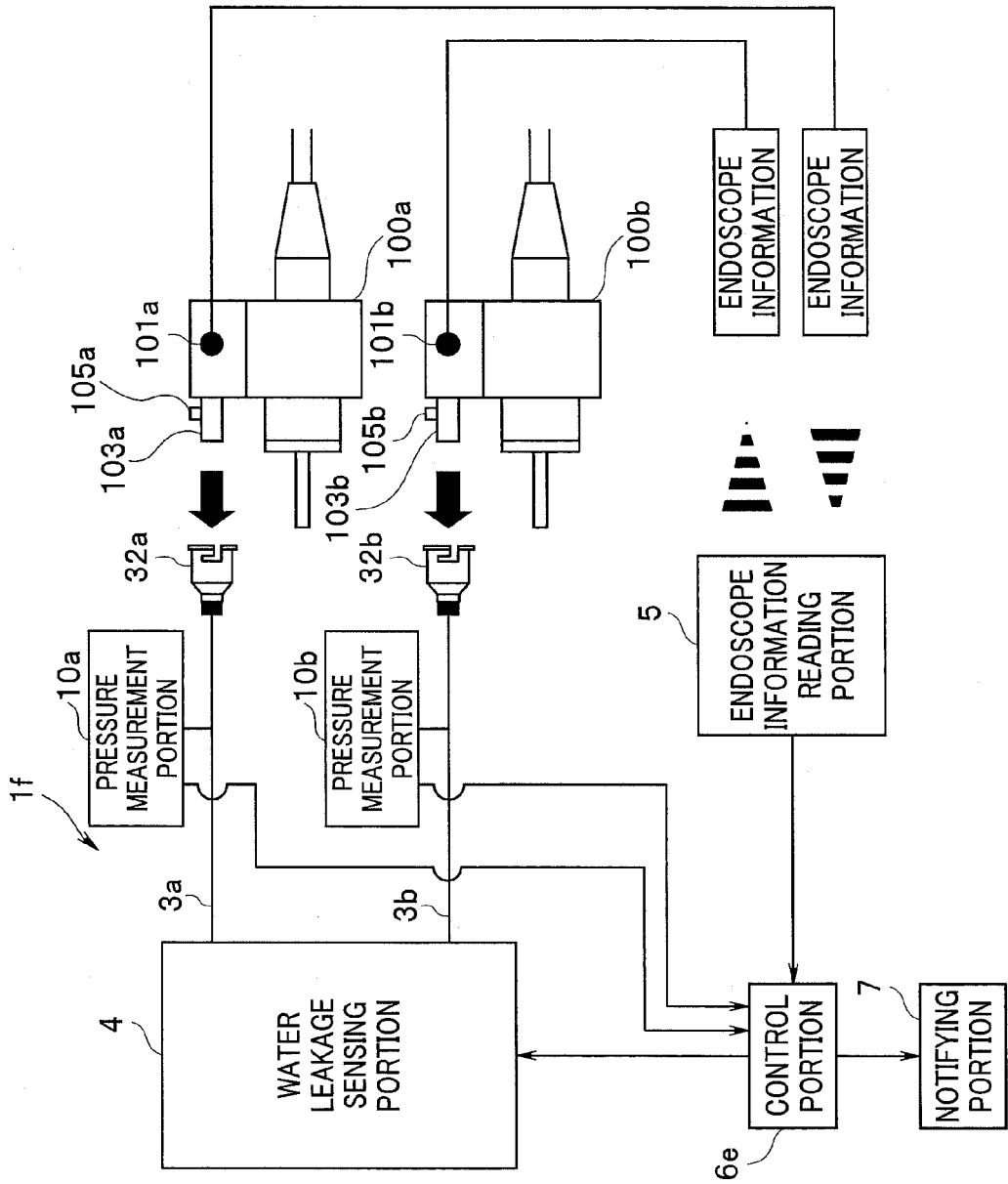
FIG. 16 is a diagram showing a configuration of a water leakage checking apparatus according to a seventh embodiment.

FIG. 16 is a diagram showing a configuration of a water leakage checking apparatus according to a seventh embodiment. It should be noted that in FIG. 16, same reference numerals are used for denoting the same components as those in FIG. 12, and descriptions thereof are omitted.

As shown in FIG. 16, a water leakage checking apparatus 1f includes a control portion 6e instead of the control portion 6d in FIG. 12 as well as the housing portions 33a and 33b are removed from FIG. 12.

When a power supply is turned on, the control portion 6e outputs an instruction to the water leakage sensing portion 4 for setting the conduit 3a to a predetermined pressure P1, and the conduit 3b to a predetermined pressure P2. It is noted that the predetermined pressure P1 is pressure under which a human force is enough for attaching the endoscope 100a to the attachment portion 32a. Also, the predetermined pressure P2 is pressure under which the endoscope 100a cannot be attached to the attachment portion 32a by a human force. The water leakage sensing portion 4 supplies gas such as air from a pump or the like, not shown, to the conduits 3a and 3b based on an instruction from the control portion 6e.

When the control portion 6e senses that the conduit 3a reaches the predetermined pressure P1 based on a measurement value from the pressure measurement portion 10a, for example, the control portion 6e closes an electromagnetic valve, not shown, provided in the conduit 3a to maintain the pressure in the conduit 3a to the predetermined pressure P1. Also, when the control portion 6e senses that the conduit 3b reaches the predetermined pressure P2 based on a measurement value from the pressure measurement portion 10b, the control portion 6e maintains the pressure in the conduit 3b to the predetermined pressure P2.

Then, if the endoscope information reading portion 5 reads the endoscope information on the endoscope 100a, the control portion 6e causes the notifying portion 7 to notify the checker to attach the endoscope 100a to the attachment portion 32a, the pressure in which is maintained at the predetermined pressure P1, under which a human force is enough for the attachment.

Now, an operation of the water leakage checking apparatus 1f having such a configuration will be described with reference to FIG. 17.

Figure 17:
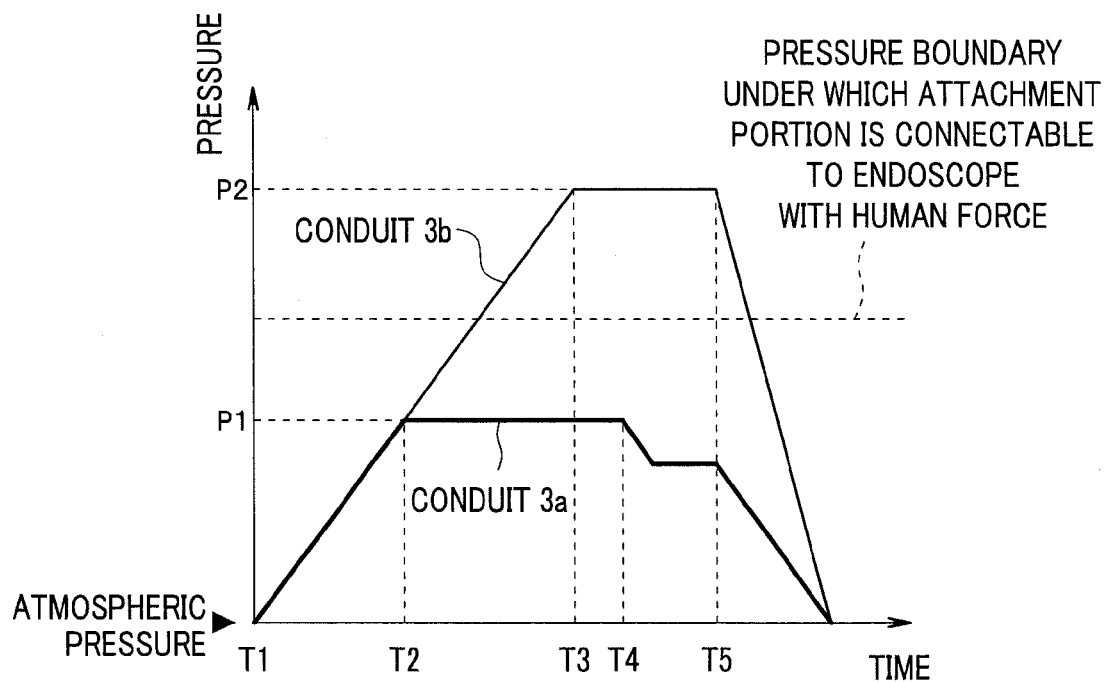
FIG. 17 is a diagram for illustrating an operation of a water leakage checking apparatus 1f according to the seventh embodiment.

FIG. 17 is a diagram for illustrating the operation of the water leakage checking apparatus 1f according to the seventh embodiment.

First, once the checker turns on a power supply, not shown, of the water leakage checking apparatus 1f at a time T1, the control portion 6e causes a pump to operate, not shown, of the water leakage sensing portion 4 to pressurize the conduits 3a and 3b. The control portion 6e performs sensing on a pressure value in the conduit 3a from the pressure measurement portion 10a and stops pressurizing the conduit 3a at a time T2 when the predetermined pressure P1 is achieved. Thereby, the pressure in the conduit 3a is maintained to the predetermined pressure P1.

Then, the control portion 6e causes the pump to operate also after the time T2 to further pressurize the conduit 3b. The control portion 6e performs sensing on a pressure value in the conduit 3b from the pressure measurement portion 10b and stops pressurizing the conduit 3b at a time T3 when the predetermined pressure P2 is achieved. Thereby, the pressure in the conduit 3b is maintained to the predetermined pressure P2.

The checker causes the endoscope information reading portion 5 to read the endoscope information recorded on the ID chip 101a of the endoscope 100a. The control portion 6e allows the notifying portion 7 to notify the checker to connect the endoscope 100a to the attachment portion 32a, to which the endoscope 100a can be attached. Based on the information of which the checker is notified by the notifying portion 7, the checker attaches the endoscope 100a to the attachment portion 32a at a time T4. If the checker attempts to attach the endoscope 100a to the attachment portion 32b, since the conduit 3b has the predetermined pressure P2, at which the attachment cannot be achieved by a human force, erroneous connection cannot be carried out. If the checker attaches the endoscope 100a to the attachment portion 32a, since the inside of the endoscope 100a communicates with the conduit in the attachment portion 32a, the pressure in the conduit 3a is lowered. The control portion 6e detects the pressure change and recognizes that the endoscope 100a has been correctly attached to the attachment portion 32a.

Then, at a time T5, the checker causes the endoscope information reading portion 5 to read the endoscope information recorded on the ID chip 101b of the endoscope 100b. When the control portion 6e receives the endoscope information from the endoscope information reading portion 5 (as input), the control portion 6e decompresses the conduits 3a and 3b to the atmospheric pressure. Thereby, the checker is allowed to attach the endoscope 100b to the attachment portion 32b connected with the conduit 3b. Then, the checker attaches the endoscopes 100a and 100b to the attachment portion 32a and 32b, respectively and carries out the water leakage checking similarly as in the fifth embodiment.

As hereinbefore described, the water leakage checking apparatus 1f pressurizes one of the conduits 3a and 3b to the predetermined pressure P2, under which the attachment cannot be achieved by a human force, thereby disenabling attachment of an endoscope to one of the attachment portions 32a and 32b. As a result, the water leakage checking apparatus 1f can reliably prevent erroneous connection.

Further, the mechanical constitution of the water leakage checking apparatus 1f can be simplified compared with the water leakage checking apparatus 1d and 1e in the fifth and the sixth embodiments, so that the water leakage checking apparatus 1f can be provided more inexpensively.

The present invention is not limited to the aforementioned embodiments, and a variety of variations and modifications can be made without departing from the gist of the present invention.

What is claimed is:
1. A water leakage checking apparatus comprising:
a plurality of attachment portions for attaching an endoscope;
a water leakage sensing portion that communicates with the plurality of attachment portions and simultaneously carries out a plurality of items of a water leakage check menu, the plurality of items being different from each other for the plurality of attachment portions;

an endoscope information reading portion that reads endoscope information from the endoscope;

a control portion that, in a state where the endoscope is not attached, determines an item of the water leakage check menu based on the endoscope information which corresponds to the endoscope from which the endoscope information is read, assigns a determined item of the water leakage check menu to one of the plurality of attachment portions, and outputs attachment portion identifying information for identifying an assigned attachment portion; and a notifying portion that notifies the attachment portion identifying information outputted from the control portion to an outside of the water leakage checking apparatus in the state where the endoscope is not attached.

2. The water leakage checking apparatus according to claim 1, wherein the notifying portion is a display, and the display displays a name or a position of the assigned attachment portion.

3. The water leakage checking apparatus according to claim 1, wherein the notifying portion is a lighting portion installed in each of the plurality of attachment portions, and only the lighting portion installed in the assigned attachment portion illuminates or blinks.

4. The water leakage checking apparatus according to claim 1, further comprising a connection sensing portion for sensing that the endoscope is connected to at least one of the plurality of attachment portions, wherein the control portion determines, based on a sensing result from the connection sensing portion, whether or not the endoscope is connected to the assigned attachment portion, and the notifying portion notifies an error if the control portion determines that the endoscope is connected to any of the plurality of attachment portions to which the item of the menu is not assigned.

5. The water leakage checking apparatus according to claim 1, wherein each of the plurality of attachment portions includes an opening/closing portion that opens or closes a notch portion used for connection of the endoscope, and the control portion opens only an opening/closing portion included in the assigned attachment portion.

6. The water leakage checking apparatus according to claim 1, further comprising a housing portion in which each of the plurality of attachment portions is housed, and the control portion controls to push out only the assigned attachment portion from the housing portion.

7. The water leakage checking apparatus according to claim 1, wherein the control portion pressurizes one of a plurality of conduits connected to the plurality of attachment portions to a first predetermined pressure and pressurizes another conduit to a second predetermined pressure which is higher than the first predetermined pressure.

* * * * *